United States Patent
Wang et al.

(10) Patent No.: US 10,429,478 B2
(45) Date of Patent: Oct. 1, 2019

(54) PUSH-BUTTON VESSEL WALL MRI WITH 3D SCOUT SCAN

(71) Applicants: KONINKLIJKE PHILIPS N.V., Eindhoven (NL); UNIVERSITY OF WASHINGTON, Seattle, WA (US)

(72) Inventors: Jinnan Wang, Eindhoven (NL); Peter Boernert, Eindhoven (NL); Chun Yuan, Eindhoven (NL)

(73) Assignees: UNIVERSITY OF WASHINGTON, Seattle, WA (US); KONINKLIJKE PHILIPS N.V., Eindhoven (NL)

( * ) Notice: Subject to any disclaimer, the term of this patent is extended or adjusted under 35 U.S.C. 154(b) by 729 days.

(21) Appl. No.: 14/917,294

(22) PCT Filed: Sep. 3, 2014

(86) PCT No.: PCT/IB2014/064215
§ 371 (c)(1),
(2) Date: Mar. 8, 2016

(87) PCT Pub. No.: WO2015/033271
PCT Pub. Date: Mar. 12, 2015

(65) Prior Publication Data
US 2016/0216354 A1    Jul. 28, 2016

Related U.S. Application Data

(60) Provisional application No. 61/875,273, filed on Sep. 9, 2013.

(51) Int. Cl.
G01R 33/563 (2006.01)
A61B 5/055 (2006.01)
(Continued)

(52) U.S. Cl.
CPC .......... G01R 33/5635 (2013.01); A61B 5/055 (2013.01); G01R 33/34 (2013.01);
(Continued)

(58) Field of Classification Search
CPC ...... A61B 5/055; G01R 33/34; G01R 33/385; G01R 33/543; G01R 33/5602; G01R 33/5635
See application file for complete search history.

(56) References Cited

U.S. PATENT DOCUMENTS 5,271,399 A    12/1993  Listerud et al.
6,397,096 B1    5/2002  Liu et al.
(Continued)

FOREIGN PATENT DOCUMENTS

WO    2010116772    10/2010

OTHER PUBLICATIONS

Wu et al "Sub-Millimeter Isotropic MRI for Segmentation of Subcortical Brain Regions and Brain Visualization" Journal of Magnetic Resonance Imaging, 31: p. 980-986 (2010).
(Continued)

*Primary Examiner* — Michael T Rozanski

(57) ABSTRACT

A medical system (10) and method (100) image a vessel wall automatically. A scout scan of a patient for localizing a target vessel of the patient is automatically performed (102) using magnetic resonance (MR). The scout scan is three-dimensional (3D) and isotropic. An MR data set of the scout scan is automatically reconstructed (104) into foot-to-head (FH), left-to-right (LR) and posterior-to-anterior (PA) projections. A 3D imaging volume (16) encompassing the target vessel is automatically determined (106) from the projections, and a diagnostic scan of the 3D imaging volume (16) is performed (108) using MR.

20 Claims, 4 Drawing Sheets

(51) Int. Cl.
G01R 33/34 (2006.01)
G01R 33/54 (2006.01)
G01R 33/56 (2006.01)
G01R 33/385 (2006.01)

(52) U.S. Cl.
CPC ......... *G01R 33/385* (2013.01); *G01R 33/543* (2013.01); *G01R 33/5602* (2013.01)

(56) References Cited

U.S. PATENT DOCUMENTS

| | | |
|---|---|---|
| 2003/0173965 A1 | 9/2003 | Oesingmann |
| 2005/0038336 A1 | 2/2005 | Nimsky |
| 2007/0276221 A1 | 11/2007 | Warntjes |
| 2010/0331664 A1 | 12/2010 | Graessner |
| 2011/0206260 A1 | 8/2011 | Bergmans |
| 2011/0228998 A1 | 9/2011 | Vaidya |
| 2011/0304333 A1 | 12/2011 | Rapoport |
| 2013/0154646 A1 | 6/2013 | Nitta |

OTHER PUBLICATIONS

Balu et al, Serial MRI of Carotid Plaque Burden: Influence of Sujbect Repositioning . . . Magnetic Resonance in Medicine 2007; vol. 57 p. 592-599.

PUSH-BUTTON VESSEL WALL MRI WITH 3D SCOUT SCAN

CROSS REFERENCE TO RELATED APPLICATIONS

This application is a U.S. national phase application of International Application No. PCT/IB2014/064215, filed on Sep. 3, 2014, which claims the benefit of U.S. provisional Application Ser. No. 61/875,273 filed on Sep. 9, 2013 and is incorporated herein by reference.

The present application relates generally to magnetic resonance (MR) imaging. It finds particular application in conjunction with vessel wall imaging, and will be described with particular reference thereto. However, it is to be understood that it also finds application in other usage scenarios and is not necessarily limited to the aforementioned application.

Vessel wall imaging based on MR, such as MR based plaque imaging, has a number of advantages over vessel wall imaging based on other imaging modalities, such as computed tomography (CT) and ultrasound (US). These advantages include better soft tissue contrast and more flexible image contrast. Despite these advantages, the clinical adoption of MR based vessel wall imaging has been relatively slow. Among other things, MR based vessel wall imaging is slow and has a complex workflow compared to vessel wall imaging based on other imaging modalities. Recent developments in hardware and imaging sequences have reduced the traditional forty-five minute imaging time by up to two-thirds. For example, regular bilateral carotid artery imaging can now be performed in as little as fifteen minutes due to these recent developments. Nonetheless, the complex imaging workflow remains a challenge for broader clinical adoption of MR based vessel wall imaging.

With reference to FIGS. 1A-D, a known workflow for MR based vessel wall imaging is illustrated with the carotid artery. The workflow includes three to four localizer and/or scout scans before a diagnostic scan can be performed. The first scan is a scout scan, an example of which is illustrated in FIG. 1A. The subsequent scans include a bright-blood time-of-flight (TOF) scan and an oblique black-blood scan. Examples of these two scans are correspondingly illustrated in FIGS. 1B and 1C. Depending on the purpose of the diagnostic scan, an extra oblique black-blood scan might be needed to capture the sagittal black-blood images from both sides of the carotid artery. After the three to four localizer and/or scout scans, a diagnostic scan is performed, an example of which is illustrated in FIG. 1D. The workflow is described in greater detail in Balu et al. Serial MRI of carotid plaque burden: influence of subject repositioning on measurement precision. Magnetic Resonance in Medicine 2007. 57:592-599.

One of the reasons the workflow is complex is that it requires numerous scans. The scout scan and the bright-blood TOF scan are used to identify the location of the target vessel. Further, the one or more oblique black-blood scans are used to achieve reproducible diagnostic scans, because the location of the bifurcation is used as the landmark in the diagnostic scans. The oblique black-blood scans cannot be easily replaced by the bright-blood TOF scan, because the resolution in the foot-to-head (FH) direction of the oblique black-blood scans is approximately 0.6 millimeters (mm), whereas the resolution in the FH direction of the bright-blood TOF is approximately 2 mm. Further, using a black-blood sequence is more reliable than a bright-blood sequence. Adding to the complexity of the workflow, each of the scans requires manual interaction from a skilled technician. Hence, successful completion of all the scans requires extensive training and even then is still prone to errors.

The present application provides a new and improved system and method which overcome these problems and others.

In accordance with one aspect, a medical system for vessel wall imaging is provided. The medical system includes a controller including a scout unit. The scout unit performs a scout scan of a patient for localizing a target vessel of the patient using magnetic resonance (MR). The scout scan is three-dimensional (3D) and isotropic. The controller further includes a scout reconstruction unit reconstructing an MR data set of the scout scan into foot-to-head (FH), left-to-right (LR) and posterior-to-anterior (PA) projections. Further, the controller includes an imaging-volume unit determining a 3D imaging volume encompassing the target vessel from the projections and a diagnostic unit performing a diagnostic scan of the 3D imaging volume using MR.

In accordance with another aspect, a medical method for vessel wall imaging is provided. A scout scan of a patient for localizing a target vessel of the patient is automatically performed using magnetic resonance (MR). The scout scan is three-dimensional (3D) and isotropic. An MR data set of the scout scan is automatically reconstructed into foot-to-head (FH), left-to-right (LR) and posterior-to-anterior (PA) projections. A 3D imaging volume encompassing the target vessel is automatically determined from the projections. A diagnostic scan of the 3D imaging volume is performed using MR.

In accordance with another aspect, a medical system for vessel wall imaging is provided. The medical system includes a magnetic resonance (MR) scanner performing a scout scan of a patient for localizing a target vessel of the patient using magnetic resonance (MR). The scout scan is three-dimensional (3D) and isotropic. The medical system further includes a reconstruction processor reconstructing an MR data set of the scout scan into foot-to-head (FH), left-to-right (LR) and posterior-to-anterior (PA) projections. Even more, the medical system includes a controller automatically determining a 3D imaging volume encompassing the target vessel from the projections. The MR scanner further performs a diagnostic scan of the 3D imaging volume.

One advantage resides in magnetic resonance (MR) based vessel wall imaging that is fully automatic (i.e., requires no user input) except for initiation.

Another advantage resides in a reduction in the duration of localizer and/or scout scanning.

Another advantage resides in a reduction in the number of localizer and/or scout scans from three or four to only one.

Another advantage resides in no compromise in registration accuracy between localizer and/or scans and diagnostic scans.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

The known approach to magnetic resonance (MR) based vessel wall imaging comprises a complex workflow, which usually requires three to four localizer and/or scout scans before a diagnostic scan can be performed. Further, planning the scans requires extensive training and can be error-prone. The present application uses advancements in hardware and three-dimensional (3D) imaging to provide an enhanced approach to vessel wall imaging that comprises a workflow that reduces the required human interaction. The workflow can include as few user interactions as a simple click or push of a button (e.g., a "start" button).

Figure 2:
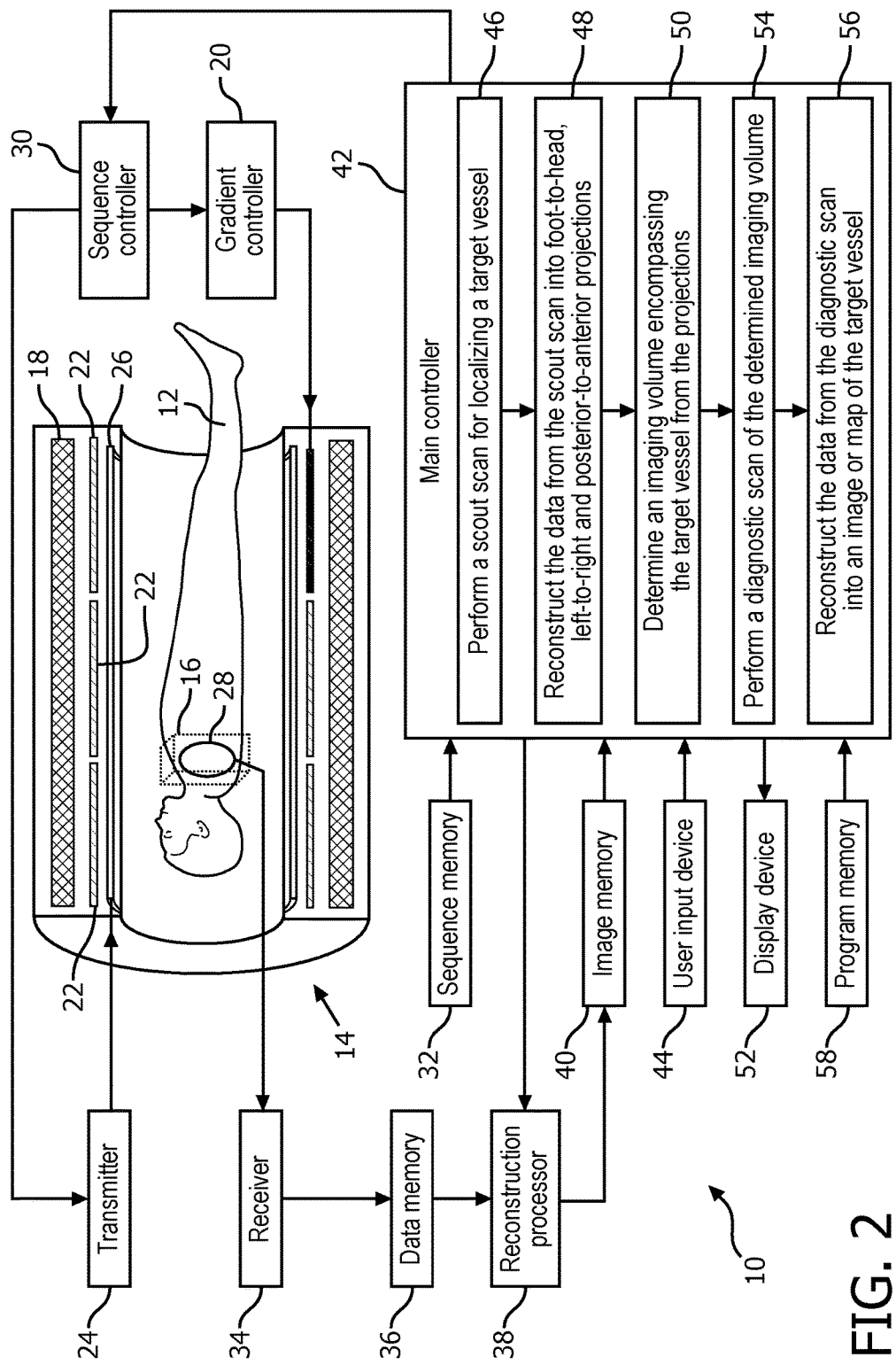
FIG. 2 illustrates an MR imaging system employing an enhanced approach to vessel wall imaging.

With reference to FIG. 2, an imaging system 10 utilizes MR and an enhanced approach to vessel wall imaging to generate one or more diagnostic images of a target vessel, such as the carotid artery, of a patient 12. The system 10 includes a scanner 14 defining an imaging (or scan) volume 16 sized to accommodate the target vessel. A patient support can be employed to support the patient 12 and to position the target vessel near the isocenter of the imaging volume 16.

The scanner 14 includes a main magnet 18 that creates a strong, static $B_0$ magnetic field extending through the imaging volume 16. The main magnet 18 typically employs superconducting coils to create the static $B_0$ magnetic field. However, the main magnet 18 can also employ permanent or resistive magnets. Insofar as superconducting coils are employed, the main magnet 18 includes a cooling system, such as a liquid helium cooled cryostat, for the superconducting coils. The strength of the static $B_0$ magnetic field is commonly one of 0.23 Tesla, 0.5 Tesla, 1.5 Tesla, 3 Tesla, 7 Tesla, and so on in the imaging volume 16, but other strengths are contemplated.

A gradient controller 20 of the scanner 14 is controlled to superimpose magnetic field gradients, such as x, y and z gradients, on the static $B_0$ magnetic field in the imaging volume 16 using a plurality of magnetic field gradient coils 22 of the scanner 14. The magnetic field gradients spatially encode magnetic spins within the imaging volume 16. Typically, the plurality of magnetic field gradient coils 22 include three separate magnetic field gradient coils spatially encoding in three orthogonal spatial directions.

Further, one or more transmitters 24, such as a transceiver, are controlled to transmit $B_1$ resonance excitation and manipulation radiofrequency (RF) pulses into the imaging volume 16 with one or more transmit coil arrays, such as a whole body coil 26 and/or a surface coil 28, of the scanner 14. The $B_1$ pulses are typically of short duration and, when taken together with the magnetic field gradients, achieve a selected manipulation of magnetic resonance. For example, the $B_1$ pulses excite the hydrogen dipoles to resonance and the magnetic field gradients encode spatial information in the frequency and phase of the resonance signal. By adjusting the RF frequencies, resonance can be excited in other dipoles, such as phosphorous, which tend to concentrate in known tissues, such as bones.

A sequence controller 30 controls the gradient controller 20 and/or the transmitters 24 according to imaging sequences to produce spatially encoded MR signals within the imaging volume 16. An imaging sequence defines a sequence of $B_1$ pulses and/or magnetic field gradients. Further, the imaging sequences can be received from a device or system being remote or local to the sequence controller, such as a sequence memory 32.

One or more receivers 34, such as a transceiver, receive the spatially encoded magnetic resonance signals from the imaging volume 16 and demodulate the received spatially encoded magnetic resonance signals to MR data sets. The MR data sets include, for example, k-space data trajectories. To receive the spatially encoded magnetic resonance signals, the receivers 34 use one or more receive coil arrays, such as the whole body coil 26 and/or the surface coil 28, of the scanner 14. The receivers 34 typically store the MR data sets in a data memory 36.

A reconstruction processor 38 reconstructs the MR data sets into MR images or maps of the imaging volume 16. This includes, for each MR signal captured by the MR data sets, spatially decoding the spatial encoding by the magnetic field gradients to ascertain a property of the MR signal from each spatial region, such as a pixel or voxel. The intensity or magnitude of the MR signal is commonly ascertained, but other properties related to phase, relaxation time, magnetization transfer, and the like can also be ascertained. The MR images or maps are typically stored in an image memory 40.

A main controller 42 controls the reconstruction processor 38 and the sequence controller 30 to generate one or more diagnostic images of the target vessel using one or more scans of the target vessel and an enhanced approach to vessel wall imaging. For each scan, the target vessel is positioned within the imaging volume 16. For example, the patient 12 is positioned on the patient support. The surface coil 28 is then positioned on the patient 12 and the patient support moves the ROI into the imaging volume 16. The size of the imaging volume 16 can vary between scans.

Once the target vessel is positioned within the imaging volume 16, the main controller 42 controls the sequence controller 30 according to scan parameters, such as number of slices, and provides the sequence controller 30 with an imaging sequence. The imaging sequence can, for example, be stored in the sequence memory 32. As noted above, an imaging sequence defines a sequence of $B_1$ pulses and/or magnetic field gradients that produce spatially encoded MR signals from the imaging volume 16. Further, the main controller 42 can control the receivers 34 according to scan parameters. For example, the main controller 42 can adjust the gain of the receivers 34.

Figure 1A:
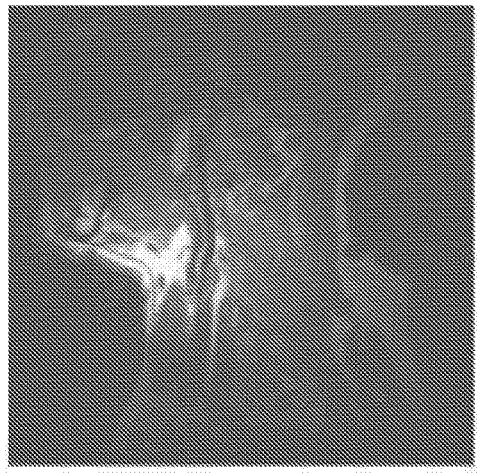
FIG. 1A illustrates a scout scan for a known approach to magnetic resonance (MR) based vessel wall imaging.
Figure 1B:
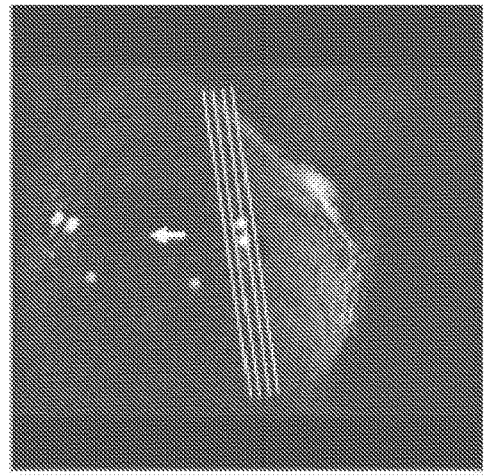
FIG. 1B illustrates a bright-blood time-of-flight (TOF) scan for the approach of FIG. 1A.
Figure 1C:
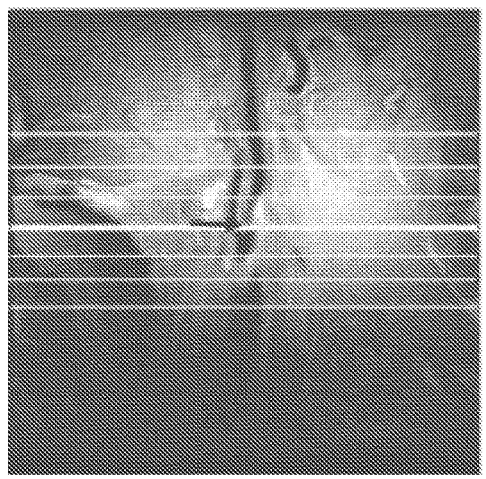
FIG. 1C illustrates an oblique black-blood scan for the approach of FIG. 1A.
Figure 1D:
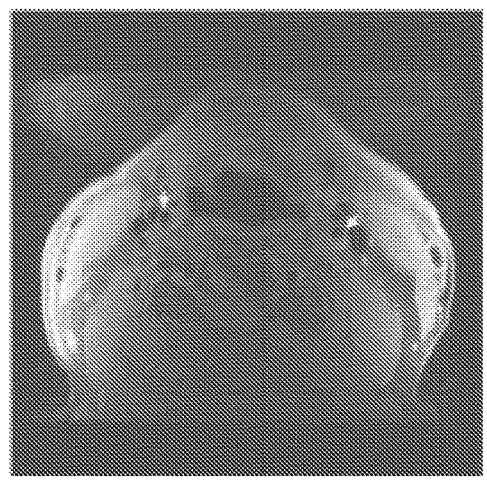
FIG. 1D illustrates a diagnostic scan for the approach of FIG. 1A.

As discussed above, the known approach to vessel wall imaging includes three to four localizer and/or scout scans before a diagnostic scan can be performed. The first scan is a scout scan, an example of which is illustrated in FIG. 1A. The subsequent scans include a bright-blood time-of-flight (TOF) scan and an oblique black-blood scan. Examples of these two scans are correspondingly illustrated in FIGS. 1B and 1C. Depending on the purpose of the diagnostic scan, an extra oblique black-blood scan might be needed. After the three to four localizer and/or scout scans, a diagnostic scan is performed, an example of which is illustrated in FIG. 1D The present application employs an enhanced approach to vessel wall imaging that includes only a single localizer and/or scout scan before an isotropic diagnostic scan is performed. Only initiation (e.g., selecting a "start" button) of the localizer and/or scout scan is needed from the user of the MR system 10. All other steps can be automatically implemented.

Vessel wall imaging according to the present application advantageously achieves this simplified workflow by combining the scout scan and the bright-blood time-of-flight (TOF) scan into a bright-blood scan. The bright-blood scan has coverage selected such that it is assured to cover a volume larger than the target vessel (e.g., twice the volume of the target volume) and within which the target vessel is located. Further, the isotropic resolution matrix of the diagnostic scan allows for flexible image reconstruction in any direction, thus maintaining the same registration accuracy no matter where the slab (or slice) is positioned and the thus eliminating the need for the one or more oblique black-blood scans.

The main controller 42 carries out the enhanced approach to vessel wall imaging in response to user input (e.g., input from a user input device 44, such as a push of a button). The enhanced approach includes performing by a scout unit or module 46 a bright-blood scout scan covering an imaging volume 16 within which the vessel wall is known to be located. The imaging volume 16 is suitably sized large enough (e.g., 10-15 centimeters (cm) in the foot-to-head (FH) direction and the limits of the field of view for the other directions) to include the target vessel centered on the approximately known location of the target vessel. In this sense, the coverage area of the bright-blood scan is large. The bright-blood scan is further isotropic, 3D and high resolution (e.g., 1-1.5 mm). The bright-blood scan can be generated using any technique, such as time-of-flight (TOF) or other magnetic resonance angiogram (MRA) techniques.

Figure 3A:
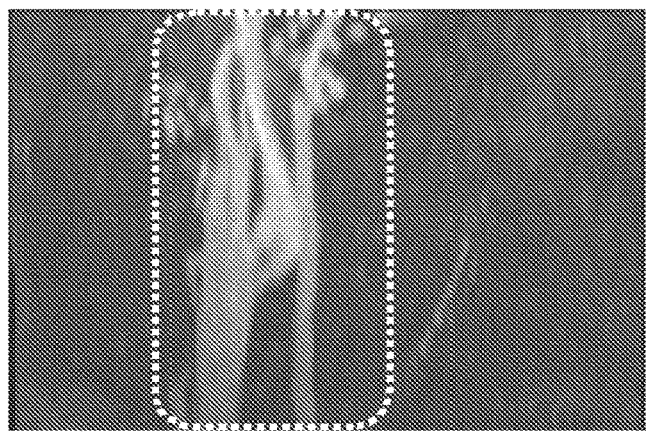
FIG. 3A illustrates a left-to-right (LR) projection of a bright-blood scan.
Figure 3B:
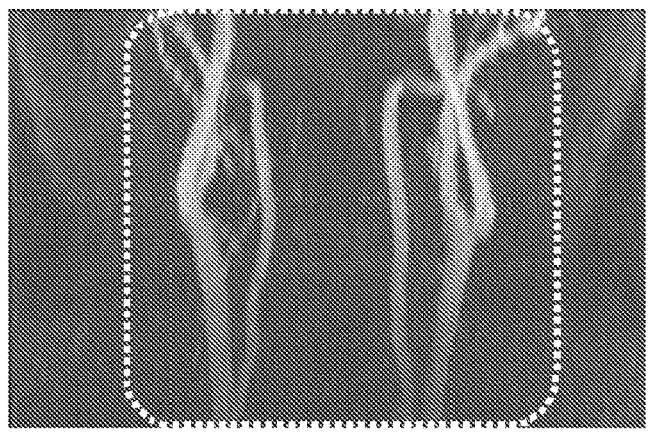
FIG. 3B illustrates an anterior-to-posterior (AP) projection of the bright-blood scan of FIG. 3A.
Figure 3C:
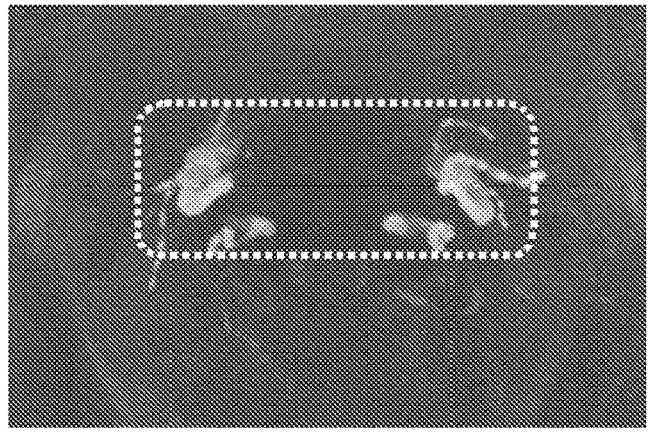
FIG. 3C illustrates a foot-to-head (FH) projection of the bright-blood scan of FIG. 3A.

After performing the bright-blood scan, a scout-reconstruction unit or module 48 uses the reconstruction processor 38 to automatically reconstruct the corresponding MR data set into FH, left-to-right (LR) and posterior-to-anterior (PA) bright-blood projections using known techniques. In other words, a 3D image or map of the bright-blood scan is projected to two-dimensional (2D) images or maps (i.e., projections). FIGS. 3A-C illustrate examples of these projections. FIG. 3A illustrates an LR projection, FIG. 3B illustrates an AP projection and FIG. 3C illustrates an FH projection.

From the projections, a 3D imaging volume is automatically determined by an imaging-volume unit or module 50. This includes automatically determining a 2D imaging volume in each of the projections. The 2D imaging volumes are suitably sized to include the complete target vessel and at the same time minimize the volume to maintain time efficiency. One approach to determining the 2D imaging volumes employs edge detection with signal intensity to identify the edges of the target vessel. Margins, such as 5-10 cm, are then added around the detected edges to define the 2D imaging volumes. The dashed lines of FIGS. 3A-C illustrate examples of 2D imaging volumes which were automatically determined. In some embodiments, the 2D imaging volumes are displayed to a user of the MR system 10 on a display device 52 (e.g., in the manner illustrated in FIGS. 3A-C) to allow the user to modify the 2D imaging volumes using a user input device 44.

Once the 2D imaging volumes are determined, they are combined into the 3D imaging volume. The 2D imaging volumes can be combined by reverse projecting each of the 2D imaging volumes into a 3D imaging volume (i.e., a reverse projection). In the reverse projection, the corresponding 2D imaging volume extends infinitely in the new, third dimension. The intersection of the reverse projections is then determined. It is this intersection that represents the 3D imaging volume. Hence, the 2D imaging volumes of the LR, AP and FH projections define the shapes of the 3D imaging volume in the corresponding directions. For example, the 2D imaging volume for the LR projection defines the shape of the 3D imaging volume in the LR direction.

One or more diagnostic scans of the 3D imaging volume are subsequently performed by a diagnostic unit or module 54. The diagnostic scans are isotropic and high resolution (e.g., less than 0.7 mm). Further, the diagnostic scans can use acceleration techniques and/or folded imaging techniques. Each of the diagnostic scans can be T1 weighted, T2 weighted or both T1 and T2 weighted. Further, each of the diagnostic scans can be bright- or black-blood scans depending upon the application of the diagnostic scan. Examples of imaging sequences that can be used for the diagnostic scans include a 3D MERGE black-blood imaging sequence and a 3D SNAP black- or bright-blood imaging sequence. In some embodiments, where time is limited, the bright-blood imaging scan can be used as a diagnostic scan.

The MR data sets from the diagnostic scans are reconstructed by a diagnostic-reconstruction unit or module 56 using the reconstruction processor 38 into images or maps of the target vessel. These images or maps can be displayed on the display device 52 or otherwise presented to a user of the MR system 10. Additionally, these images or maps can be stored in the image memory 40.

The main controller 42 can carry out the enhanced approach to vessel wall imaging by software, hardware or both. In that regard, each of the units or modules 46, 48, 50, 54, 56 can be carried out by a unit or module of software, hardware or both. For each of the software units or modules, the main controller 42 includes at least one processor executing the software. Where the units or modules 46, 48, 50, 54, 56 are all software, the main controller 42 is at least one processor executing the software. The processor executable instructions of software are suitably stored on a program memory 58, which can be local or remote from the main controller 42. According to a preferred embodiment, the main controller 42 is one or more processors programmed to carry out the enhanced approach to vessel wall imaging. In such embodiments, the processors typically execute processor executable instructions embodying the enhanced approach.

Further, notwithstanding that the reconstruction processor 38 and the sequence controller 30 were illustrated as external to the main controller 42, it is to be appreciated that one or both of these components can be integrated with the main controller 42 as software, hardware or a combination of both. For example, the reconstruction processor 38 can be integrated with the main controller 42 as a software module executing on processors of the main controller 42.

Figure 4:
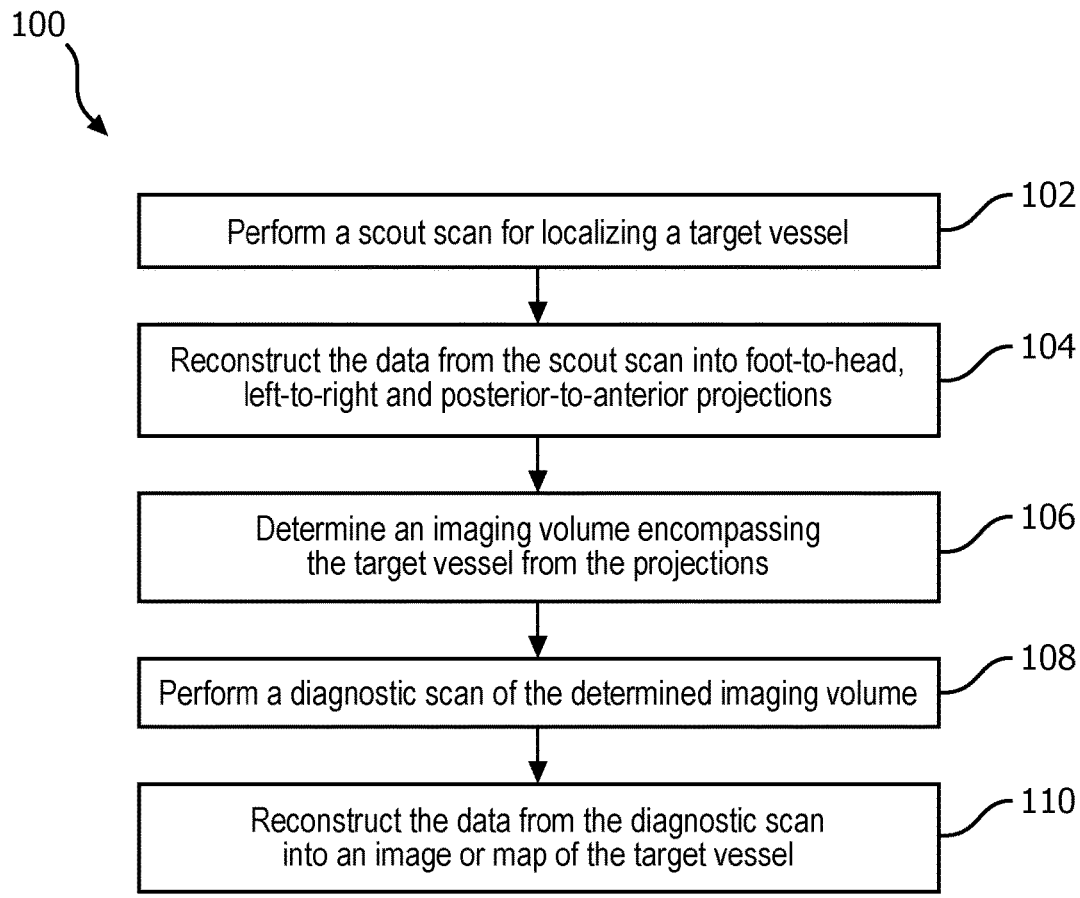
FIG. 4 is a block diagram of the enhanced approach to vessel wall imaging of FIG. 2.

With reference to FIG. 4, a block diagram 100 of the enhanced method is provided. As discussed above, the enhanced method is suitably performed by the main controller (42). According to the enhanced method, a scout scan of a patient is performed 102 (corresponding to the actions of the scout unit 46) for localizing a target vessel of the patient using magnetic resonance (MR). The scout scan is suitably three-dimensional (3D) and isotropic. The MR data set of the scout scan is reconstructed 104 (corresponding to the actions of the scout-reconstruction unit 58) into foot-to-head (FH), left-to-right (LR) and posterior-to-anterior (PA) projections, and a 3D imaging volume (16) encompassing the target vessel is automatically determined 106 (corresponding to actions of the imaging-volume unit 50) from the projections. A diagnostic scan of the 3D imaging volume (16) is performed 108 (corresponding to the actions of the diagnostic unit 54) using MR and an MR data set of the diagnostic scan is reconstructed 110 (corresponding to the actions of the diagnostic-reconstruction unit 56) into an image of the target vessel.

As used herein, a memory includes any device or system storing data, such as a random access memory (RAM) or a read-only memory (ROM). Further, as used herein, a processor includes any device or system processing input device to produce output data, such as a microprocessor, a microcontroller, a graphic processing unit (GPU), an application-specific integrated circuit (ASIC), an FPGA, and the like; a controller includes any device or system controlling another device or system; a user input device includes any device, such as a mouse or keyboard, allowing a user of the user input device to provide input to another device or system; and a display device includes any device for displaying data, such as a liquid crystal display (LCD) or a light emitting diode (LED) display.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A medical system for imaging a vessel wall of a target vessel in a patient, said medical system comprising:
   a magnetic resonance (MR) scanner;
   a display device; and
   a controller including:
      an MR control unit configured to control the MR scanner to perform a single scout scan of a patient for localizing the target vessel of the patient to produce a three-dimensional (3D), isotropic scout MR data set;
      a reconstruction unit configured to reconstruct the scout MR data set into a two-dimensional (2D) foot-to-head (FH) projection image, a 2D left-to-right (LR) projection image and a 2D posterior-to-anterior (PA) projection image;
      a diagnostic imaging-volume unit configured to determine a 3D diagnostic imaging volume encompassing the target vessel from the 2D foot-to-head, left-to-right, and posterior-to-anterior projection images;
      wherein the MR control unit is further configured to control the MR scanner to perform a diagnostic imaging scan of the target vessel of the 3D diagnostic imaging volume to produce a 3D diagnostic MR data set;
      wherein the reconstruction unit is further configured to reconstruct the 3D diagnostic MR data set into a diagnostic image of the target vessel; and
      a display control unit configured to control the display device to display the diagnostic image of the target vessel.

2. The medical system of claim 1, wherein the controller includes software and the controller includes one or more processors configured to execute the software.

3. The medical system of claim 1, wherein the scout scan is a bright-blood scan.

4. The medical system of claim 1, wherein the diagnostic imaging-volume unit is configured to:
   identifying edges of the target vessel in each of the 2D foot-to-head image, the 2D left-to-right image, and the posterior-to-anterior projection image;
   define a 2D imaging subvolume based on the identified edges in each of the 2D foot-to-head image, the left-to-right image, and the posterior-to-anterior projection image; and
   reverse project the 2D imaging subvolumes of the 2D foot-to-head image, the 2D left-to-right image, and the 2D posterior-to-anterior projection image, a 3D volume in which the 2D foot-to-head reverse projection, the 2D left-to-right reverse projection, and the 2D posterior-to-anterior reverse projection intersect defining the 3D diagnostic image volume.

5. A medical method for imaging a vessel wall, said medical method comprising:
   automatically performing a single scout scan of a patient for localizing a target vessel of the patient using magnetic resonance (MR), the scout scan generating a three-dimensional (3D), isotropic scout MR data set;
   automatically reconstructing the scout MR data set of the scout scan into 2D foot-to-head (FH) projection image, a 2D left-to-right (LR) projection image, and a 2D posterior-to-anterior (PA) projection image;
   determining a 3D diagnostic imaging volume encompassing the target vessel from the 2D foot-to-head, left-to-right, and posterior-to-anterior projection images;
   performing a diagnostic scan of the 3D diagnostic imaging volume using MR to generate a diagnostic MR data set; and
   reconstructing the diagnostic MR data set into a diagnostic image including the target vessel.

6. The medical method of claim 5, wherein at least one of:
   the scout scan is a bright-blood scan;
   the scout scan encompasses a volume extending 10-15 centimeters (cm) in a foot-to-head direction and spanning the field of view in left-to-right and posterior-to-anterior directions; and
   the resolution of the scout scan is 1-1.5 millimeters (mm).

7. The medical method of claim 5, wherein the determining includes determining a 2D imaging subvolume encompassing the target vessel in each of the foot-to-head, left-to-right, and posterior-to-anterior projection images and the diagnostic 3D imaging volume is determined from the 2D imaging subvolumes.

8. The medical method of claim 5, wherein at least one of:
   the resolution of the diagnostic image is smaller than 0.7 millimeters (mm); and
   the diagnostic image is isotropic.

9. The medical method of claim 5, wherein determining the 3D image volume includes:
   identifying edges of the target vessel in each of the 2D foot-to-head, left-to-right, and posterior-to-anterior projection images;
   defining a 2D imaging subvolume based in the identified edges in each of the 2D foot-to-head, left-to-right, and posterior-to-anterior projection images; and
   reverse projecting the 2D imaging subvolumes of the 2D foot-to-head, left-to-right, and posterior-to-anterior projection images, a 3D volume in which the foot-to-head, left-to-right, and posterior-to-anterior reverse projections intersect defining the 3D diagnostic image volume.

10. The medical method of claim 9, wherein identifying the edges of the target vessel includes using edge detection to identify the edges of the target vessel in each of the 2D foot-to-head, left-to-right, and posterior-to-anterior projection images.

11. The medical method of claim 9, wherein the target vessel edges are determined by a clinician.

12. A non-transitory computer readable medium carrying software which controls one or more processors to:
   automatically perform a single scout scan of a patient for localizing a target vessel of the patient using magnetic resonance (MR), the scout scan generating a three-dimensional (3D), isotropic scout MR data set;
   automatically reconstruct the scout MR data set of the scout scan into 2D foot-to-head (FH) projection image, a 2D left-to-right (LR) projection image, and a 2D posterior-to-anterior (PA) projection image;
   determine a 3D diagnostic imaging volume encompassing the target vessel from the 2D foot-to-head, left-to-right, and posterior-to-anterior projection images, determining the 3D image volume including:
      identifying edges of the target vessel in each of the 2D foot-to-head, left-to-right, and posterior-to-anterior projection images,
      defining a 2D imaging subvolume based in the identified edges in each of the 2D foot-to-head, left-to-right, and posterior-to-anterior projection images, and
      reverse projecting the 2D imaging subvolumes of the 2D foot-to-head, left-to-right, and posterior-to-anterior projection images, a 3D volume in which the foot-to-head, left-to-right, and posterior-to-anterior reverse projections intersect defining the 3D diagnostic image volume;
   perform a diagnostic scan of the 3D diagnostic imaging volume using MR to generate a diagnostic MR data set; and
   reconstruct the diagnostic MR data set into a diagnostic image including the target vessel.

13. A medical system for imaging a vessel wall, said medical system comprising:
   one or more processors configured to:
   control a magnetic resonance (MR) scanner to perform a single scout scan of a patient for localizing a target vessel of the patient using magnetic resonance, the scout scan producing a three-dimensional (3D) and isotropic scout MR scout data set;
   reconstruct the scout MR data set of the scout scan into three orthogonal 2D projection images;
   from the three 2D projection images, automatically determine a 3D diagnostic imaging volume encompassing the target vessel;
   control the MR scanner to perform a diagnostic scan of the 3D diagnostic imaging volume to generate a 3D MR diagnostic image data set; and
   reconstruct the 3D MR diagnostic image data set into a diagnostic image of the 3D diagnostic imaging volume.

14. The medical system of claim 13, wherein the scout scan is a bright-blood scan.

15. The medical system of claim 13, wherein the scout scan encompasses a scout volume extending 10-15 centimeters (cm) in a foot-head (FH) direction and spanning the field of view in left-right (LR) and posterior-anterior (PA) directions.

16. The medical system of claim 13, wherein the resolution of the scout scan is between 1 and 1.5 millimeters (mm) and the resolution of the diagnostic scan is better than 0.7 millimeters (mm).

17. The medical system of claim 13, wherein the MR scout data set and the 3D MR diagnostic data set are isotropic.

18. The medical system of claim 13, wherein the one or more processors are configured to determine the 3D diagnostic image volume by:
   using edge detection to identify edges of the target vessel in each of the three 2D orthogonal projection images;
   using the identified edges to define a 2D imaging subvolume in each of the orthogonal 2D projection images;
   reverse projecting the 2D imaging subvolumes of the three 2D projection images, a 3D volume in which the reverse projected 2D imaging subvolumes intersect defining the 3D diagnostic image volume.

19. The medical system of claim 13, wherein the one or more processors are configured to determine the 3D diagnostic image volume by:
   receiving an identification of edges of the target vessel in each of the orthogonal projection images;
   using the edge identifications to define a 2D imaging subvolume in each of the orthogonal 2D projection images;
   reverse projecting the three 2D imaging subvolumes of the three 2D projection images to define the 3D diagnostic image volume at an intersection of the reverse projections of three 2D imaging subvolumes.

20. The medical system of claim 13, wherein the three orthogonal 2D projection images are in a foot-head direction, a left-right direction, and a posterior-anterior direction.

* * * * *